US012406198B2

(12) United States Patent
Haycock et al.

(10) Patent No.: US 12,406,198 B2
(45) Date of Patent: Sep. 2, 2025

(54) COMPUTER-IMPLEMENTED EVENT FORECASTING AND INFORMATION PROVISION

(71) Applicant: KBC GROEP NV, Brussels (BE)

(72) Inventors: Barry Haycock, Dublin (IE); Floyd Jackson, Dublin (IE)

(73) Assignee: KBC GROEP NV, Brussels (BE)

( * ) Notice: Subject to any disclaimer, the term of this patent is extended or adjusted under 35 U.S.C. 154(b) by 944 days.

(21) Appl. No.: 17/426,426

(22) PCT Filed: Feb. 21, 2020

(86) PCT No.: PCT/EP2020/054634
§ 371 (c)(1),
(2) Date: Jul. 28, 2021

(87) PCT Pub. No.: WO2020/169807
PCT Pub. Date: Aug. 27, 2020

(65) Prior Publication Data
US 2022/0108196 A1 Apr. 7, 2022

(30) Foreign Application Priority Data

Feb. 21, 2019 (EP) .................................... 19158636

(51) Int. Cl.
*G06N 7/01* (2023.01)
*B01D 3/14* (2006.01)
(Continued)

(52) U.S. Cl.
CPC ........... *G06N 7/01* (2023.01); *G06F 18/2115* (2023.01); *G06N 5/04* (2013.01); *B01D 3/143* (2013.01);
(Continued)

(58) Field of Classification Search
CPC .. C07C 2/08; C07C 7/005; C07C 7/04; C07C 2/06; C07C 11/02; C07C 11/107;
(Continued)

(56) References Cited

U.S. PATENT DOCUMENTS 5,465,321 A    11/1995 Smyth
6,415,276 B1    7/2002 Heger et al.
(Continued)

FOREIGN PATENT DOCUMENTS

WO    2020169807 A1    8/2020

OTHER PUBLICATIONS

ISR-WO dated May 20, 2020 for parent PCT/EP/2020/054634.
(Continued)

*Primary Examiner* — Quoc A Tran
(74) *Attorney, Agent, or Firm* — Vorys, Sater, Seymour and Pease LLP

(57) ABSTRACT

A computer-implemented method, a computer system and a computer program product for event forecasting and information provision are disclosed. For each entity of a group of entities one or more events are obtained, wherein each event is associated with a category of a set of categories. A model category subset of the set of categories, and a target category subset based on the model category subset, are determined. For entities for which for each category of the target category subset an event has been obtained, a sequence of categories of the model category subset is determined, and corresponding probabilities are calculated. For a target entity, a target sequence of categories of the model category subset is determined based on the events obtained for the target entity. A target category is determined based on the
(Continued)

target sequence and the calculated probabilities. Information is provided based on the target entity and the determined target category.

13 Claims, 8 Drawing Sheets

(51) Int. Cl.
      *C07C 2/08*         (2006.01)
      *C07C 7/00*         (2006.01)
      *C07C 7/04*         (2006.01)
      *G06F 18/2115*    (2023.01)
      *G06N 5/00*         (2023.01)
      *G06N 5/02*         (2023.01)
      *G06N 5/04*         (2023.01)

(52) U.S. Cl.
     CPC ............... *C07C 2/08* (2013.01); *C07C 7/005* (2013.01); *C07C 7/04* (2013.01); *G06N 5/00* (2013.01); *G06N 5/02* (2013.01); *Y02P 20/582* (2015.11)

(58) Field of Classification Search
     CPC ......... B01D 3/143; Y02P 20/582; G06N 5/04; G06N 5/02; G06N 5/00
     See application file for complete search history.

(56) References Cited

U.S. PATENT DOCUMENTS

| | | | |
|---|---|---|---|
| 8,751,492 B1* | 6/2014 | Catane | G06Q 30/02 |
| | | | 707/748 |
| 10,067,990 B1 | 9/2018 | Boothman et al. | |
| 2016/0071126 A1 | 3/2016 | Chang et al. | |
| 2017/0140285 A1 | 5/2017 | Dotan-Cohen et al. | |
| 2017/0372347 A1 | 12/2017 | Li et al. | |
| 2018/0121431 A1* | 5/2018 | Shan | G06N 7/01 |
| 2019/0065606 A1* | 2/2019 | Jiang | G06F 7/026 |

OTHER PUBLICATIONS

Pablo Gay et al, "Sequential learning for case-based pattern recognition in complex event domains", Jan. 15, 2011 (Jan. 15, 2011), Retrieved from the Internet: URL:http://ceur-ws.org/Vol-829/paper6.pdf [retrieved on Jul. 19, 2019] the whole document.

Van Der Aalst W M P et al, "Time prediction based on process mining", Apr. 1, 2011 (Apr. 1, 2011), vol. 36, No. 2, p. 450-475, DOI: 10.1016/J.IS.2010.09.001 external link; ISSN:0306-4379 [retrieved on Sep. 18, 2010] the whole document.

* cited by examiner

COMPUTER-IMPLEMENTED EVENT FORECASTING AND INFORMATION PROVISION

TECHNICAL FIELD

The invention pertains to a computer-implemented method, a computer system and a computer program product for inference (G06N 5/04), in particular sequence pattern mining, based on knowledge representation (G06N 5/02; G06N 5/00), in particular events. The invention may be used for:

- sensor-based fault tracking in a group of apparatuses, forecasting a target fault for an apparatus, and providing information for servicing the apparatus for fault avoidance;
- tracking feature usage in a computer program product in a group of users, forecasting a target feature usage for a user, and providing tutorial information on the target feature usage to the user; and/or
- tracking interactions with a service in a group of users, forecasting a target interaction for a user, and providing information on the target interaction to the user.

BACKGROUND

U.S. Pat. No. 5,465,321 A relates to fault detection in dynamic systems. A system failure monitoring method and apparatus learn symptom-to-fault mapping from training data. The state of the system is first estimated at discrete intervals in time. A feature vector is estimated from sets of successive windows of sensor data. A pattern recognition component then models the instantaneous estimate of the posterior fault class probability given the features. A hidden Markov model is used to take advantage of temporal context and estimate class probabilities conditioned on recent past history.

U.S. Pat. No. 6,415,276 B1 relates to Bayesian belief networks for industrial processes. A method and an apparatus for diagnosis of sensors and/or processes through use of Bayesian belief networks are disclosed. More specifically, the method and apparatus achieve sensor and/or process fault detection, isolation, and accommodation.

According to the above disclosures, the history is only partially taken into account, as a hidden Markov model or a Bayesian belief network are utilized. The above disclosures therefore do not teach technical features to take lengthy histories to a sufficient level into account.

US 2016/0 071 126 A1 relates to customer journey prediction and resolution. A predictive model is disclosed in which each user is mapped onto all available user journey information corresponding to a specific business. The predictive model is analyzed to understand the characteristics, preferences, and lowest effort resolution for the user related to the services that are subscribed to by the user. The predictive model is analyzed to predict the service or collection of services for each user. Embodiments interact with, provide and receive information from, and react to and/or deliver action to the customer across channels and across services. All customer and system behavior, data, and action is tracked and coordinated and leveraged for continuous feedback and performance improvement.

US 2017/0 372 347 A1 relates to a sequence-based marketing attribution model for customer journeys. A method includes extracting subsequences from a sequence of a customer journey that includes customer interactions on different channels at different times on different topics. The method further includes measuring an effectiveness of each of the subsequences based on journey success data, by applying a statistical hypothesis testing approach. The method also includes determining a contribution of each of the customer interactions for a given one of the subsequences, by applying a sequence-based journey attribution model.

U.S. Pat. No. 10,067,990 B1 relates to a system, method and computer program for identifying significant attributes of records. A plurality of records are stored, including a plurality of events with a plurality of attributes. Further, the attributes of the events are processed, utilizing machine learning. To this end, at least one of the attributes are identified as being significant, based on the processing. Such identified at least one attribute may then be displayed.

Gay, López and Meléndez, "Sequential learning for case-based pattern recognition in complex event domains", Proceedings of the 16$^{th}$ UK Workshop on Case-Based Reasoning (UKCBR 2011), Cambridge, United Kingdom, 13 Dec. 2011, published on 20 Jan. 2012 in CEUR Workshop Proceedings (ISSN 1613-0073), Vol. 829, paper 6, http://ceur-ws.org/Vol-829/paper6.pdf, hereafter Gay (2012), discloses sequence pattern mining.

At least some of the teachings disclosed in the above recited documents suffer from an overload of information. Typically, all or most information is treated on an equal footing. Gay (2012), for example, teaches away from utilizing sequences with particularization to an actor (last sentence of section 3.1). Furthermore, in at least some of the above recited documents no or inadequate action prediction is taught. Adequate action prediction should provide for timely intervention. Furthermore, usually the resulting sequences are, except for time ordering information, devoid of further time information. Intervention is more urgent for a first apparatus for which the next fault will occur soon, e.g. tomorrow, than for a second apparatus for which the next fault will occur in the distant feature, e.g. in two years. In the latter case, intervention might not even be needed anymore, e.g. in view of the scheduled lifetime of the apparatus or an upcoming scheduled maintenance. Furthermore, in environments with limited resources, e.g. one mechanic for a whole pool of apparatuses, the limited resources have to be optimally distributed. For a pool of apparatuses, for example, this may involve minimizing overall downtime over the pool. In a general formulation, this involves maximizing the overall retainment (e.g. uptime for apparatuses) over the group of entities (e.g. pool of apparatuses) during at least an initial timespan (e.g. in view of the scheduled maintenance or scheduled lifetime of an apparatus).

The present invention aims to resolve at least some of the problems mentioned above.

SUMMARY OF THE INVENTION

In a first aspect, the present invention provides a computer-implemented method for event forecasting and information provision, according to claim 1.

In a second aspect, the present invention provides a computer system for event forecasting and information provision, according to claim 12.

In a third aspect, the present invention provides a computer program product for even forecasting and information provision, according to claim 13.

The present invention is advantageous for several reasons.

One reason concerns in particular (a) the determination of a model category subset of categories from the full set of categories in combination with (b) the calculation of probabilities for a tail category to follow a base based on the entire history in the model category subset. By reducing the full set of categories to a model category subset, the entire history within the model category subset can be modelled via a sequence, and taken into account in determining probabilities. This has to be contrasted with a hidden Markov model or a Bayesian belief network, where a time scale is inherent to the model, and only recent history is taken into account.

Another reason concerns the particular hierarchy of subset determination. In case a target category subset of categories is chosen initially, and a model category subset subsequently, the accuracy relies mainly in the inclusion or exclusion of certain categories in the model category subset, often eventually modelling certain dynamics related to categories of a target category subset insufficiently by working in a reduced model category subset. By choosing a model category subset first, and a target category subset based on the model category subset subsequently, the applicant has surprisingly found that better dynamics in the reduced model category subset may be obtained, as there is no constraint yet of the target category subset. Moreover, while it a priori appears that a target category subset based on a model category subset is inherently incomplete, the applicant has surprisingly found that accuracy does not deteriorate. This may a posteriori be attributed to the insufficient modelling of certain dynamics related to categories of a target category subset when the target category subset is determined first. In other words: both upon choosing the target category subset first and the model category subset first, not all dynamics may be captured with a reduced model category subset, while the initial determination of a model category subset and the subsequent determination of a target category subset based on the model category subset provides for better dynamics modelling overall.

At least the following distinguishing features are not disclosed in Gay (2012):
  active subgroup of entities;
  determination of the active subgroup based on average event frequencies;
  target category subset;
  determination of the target category subset from the model category subset based on time spans for initial occurrence of the categories of the model category subset.

Gay (2012) in particular teaches away from particularization to actors, cfr. the last sentence of section 3.1 of Gay (2012).

These distinguishing features with respect to Gay (2012) result in the maximization of overall retainment over the group of entities during at least an initial time span:
  Individual entities can behave differently, and may have inherent differences which are a priori not known. For apparatuses, for example, if a first fault occurs in an apparatus, a second fault can have a very high chance of occurrence; likewise, if a third fault occurs in an apparatus, a fourth fault can have a very high chance of occurrence; while it can be very unlikely that the first and the third fault occur in the same apparatus. Without particularization to entities, such differences between entities cannot be inferred. The history of a particular entity is therefore of utmost importance to predict the future of the particular entity, and may be based on similar histories of other particular entities.
  By converting events associated with time stamps into sequences, only time-order information is usually retained, but not absolute or relative time information. The target category subset creation based on time spans for initial occurrence introduces time information in the model space additional to the time ordering of events of an entity, without the need to explicitly utilize absolute or relative time stamps for predicting categories for the target entity. The target category subset instead indirectly incorporates aspects of absolute or relative time stamps, via the decision of which categories to include in the target category subset of the model category subset.
  The active subgroup of entities provides for entities for which substantial entity sequence mining can be performed. There is also an additional benefit in favoring an entity with high event frequency over an entity with the same amount of events, but with lower event frequency. Two entities with an identical history, except for the event frequency, would have an equal probability distribution for the next event category, but the urgency of handling it would be larger for the entity with higher event frequency, as it would occur sooner. Retainment over the group of entities benefits most by inferring from entities with high event frequency, i.e. with a large number of events occurring within a particular time span.

DETAILED DESCRIPTION OF THE INVENTION

Figure 1:
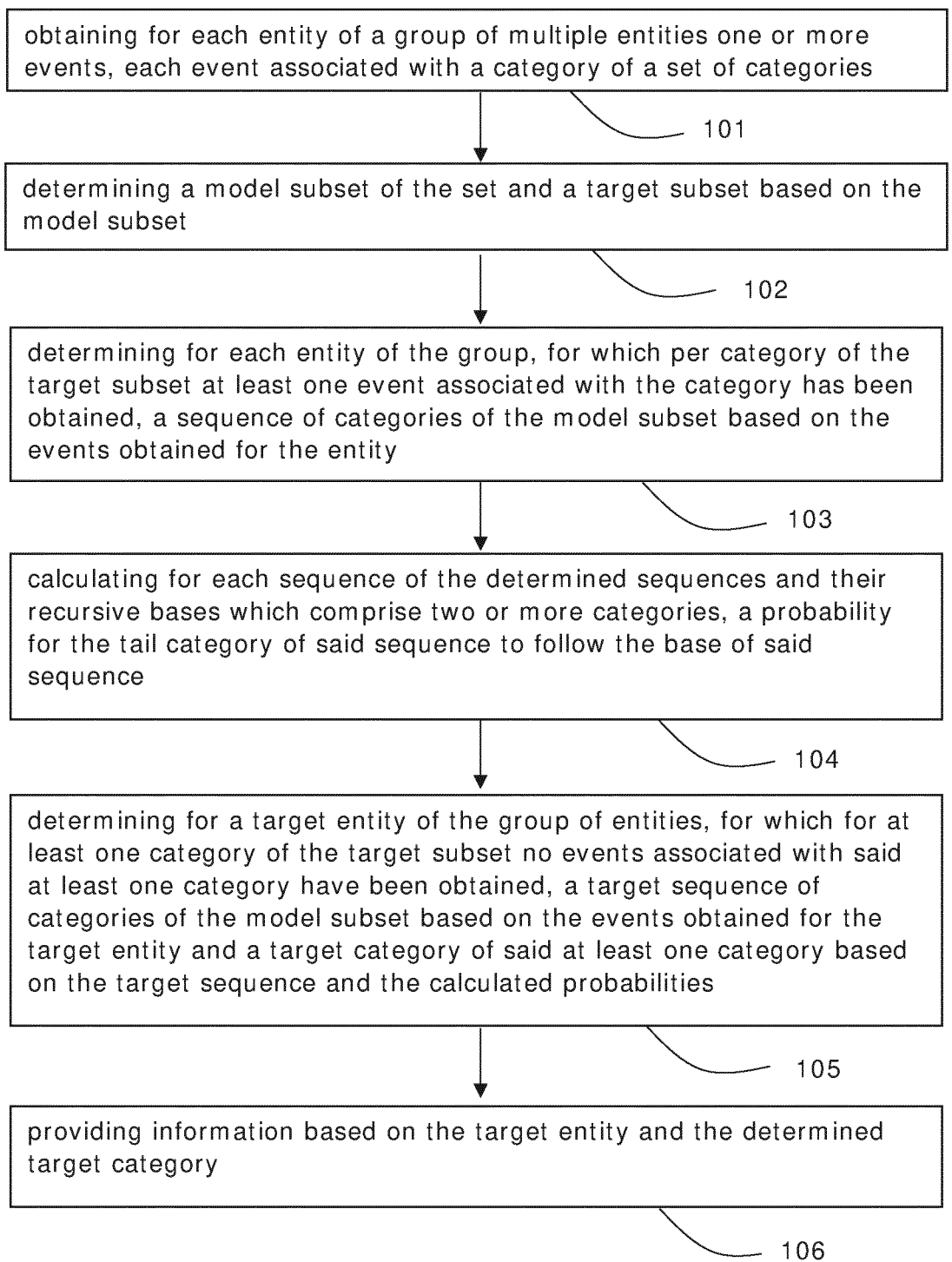
FIGS. 1, 5, 8 and 9 show schematic overviews of algorithms, according to embodiments of the present invention.

The present invention concerns a computer-implemented method (CIM), a computer system, and a computer program product (CPP) for event forecasting and information provision. The invention has been summarized in the corresponding section above. In what follows, the invention is described in detail, preferred embodiments are discussed, and the invention is illustrated by means of non-limitative examples.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", "comprises" and "comprised of" as used herein are synonymous with "include", "including", "includes" or "contain", "containing", "contains" and are inclusive or open-ended terms that specify the presence of what follows (e.g. component) and do not exclude or preclude the presence of additional, non-recited components, features, elements, members, steps, known in the art or disclosed therein.

"Based on" as used herein is synonymous with "based at least in part on" and is an inclusive or open-ended term that specifies the presence of what follows, and does not exclude or preclude the presence of additional, non-recited components, features, elements, members, steps, and the like.

A "sequence" as used herein is an ordered list of elements. A sequence comprises at least two elements. A sequence comprises a "base" and a "tail element". A sequence in particular comprises a base followed by the tail element. A base comprises one or more elements. In case a base comprises at least two elements, the base is a sequence, and the base itself comprises a base and a tail element. In a non-limitative example, a first sequence may comprise the elements E1, E4, E7, E8 and E9 in the order E1→E9→E7→E4→E8. The first sequence comprises base E1→E9→E7→E4, which is a second sequence, and tail element E8. The second sequence comprises base E1→E9→E7, which is a third sequence, and tail element E4.

A "group", "set", "collection", "list", "sequence" and the like comprising elements as used herein refers to a computer-readable, preferably digital, representation of the group, set, collection, list, sequence or the like comprising pointers to the elements, such as element ids. A set of categories hence refers to a computer-readable representation of a set comprising pointers to the categories, such as category ids. Each category is then represented by a category id. A group of apparatuses hence refers to a computer-readable representation of a group comprising pointers to the apparatuses, such as apparatus ids. Each apparatus is then represented by an apparatus id. A group of users hence refers to a computer-readable representation of a group comprising pointers to the users, such as user ids. Each user is then represented by a user id.

In a first aspect, the invention provides a CIM for event forecasting and information provision. In a second aspect, the invention provides a computer system for event forecasting and information provision, wherein the computer system comprises one or more processors, and wherein the computer system is configured for carrying out the CIM according to the first aspect of the present invention. In a third aspect, the invention provides a CPP for event forecasting and information provision, wherein the CPP comprises instructions which, when the CPP is executed by a computer, such as a computer system according to the second aspect, cause the computer to carry out the CIM according to the first aspect. The third aspect may provide a tangible non-transitory computer-readable data carrier comprising the CPP.

One of ordinary skill in the art will appreciate that the three aspects of the present invention are therefore interrelated. In what follows, explicit reference to the particular aspect may therefore be left out. Furthermore, each feature above or below may pertain to each of the aspects of the present invention, even if it has been disclosed in conjunction with a particular aspect of the present invention.

Figure 2A:
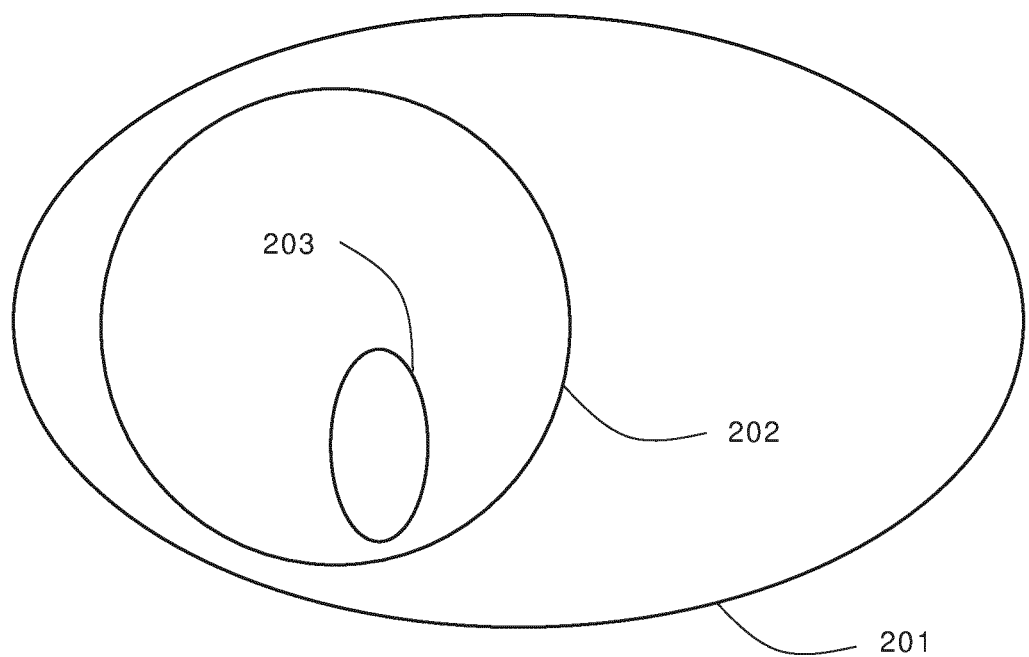
FIGS. 2A and 2B show schematic overviews of a set of categories (201), a model category subset of categories (202), and a target category subset of categories (203), according to an embodiment of the present invention.
Figure 2B:
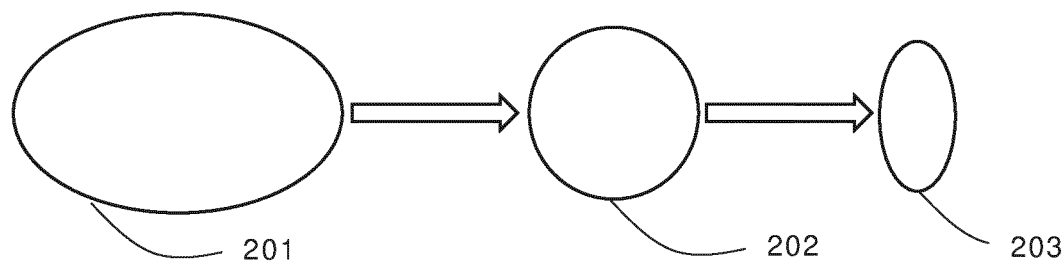

The CIM comprises several steps. Reference to FIGS. 1 and 2 is made. For each entity of a group of multiple entities, one or more events are obtained (101). Preferably, for each entity of the group of multiple entities, multiple events are obtained. Each event is associated with a category of a set of categories (201). An event may furthermore be associated with a time stamp. An event may furthermore be associated with a communication channel from a collection of communication channels. An event may in particular comprise a pointer to a category of a set of categories. An event may furthermore comprise a time stamp. An event may also comprise a pointer to a communication channel of a collection of communication channels. Preferably, for each entity of the group an average event frequency is calculated. Preferably, an active subgroup of entities is determined based on the calculated average event frequencies. A model category subset (202) of the set of categories (201) is determined (102). The set of categories (201) thereby comprises the model category subset (202). Preferably, the model category subset is determined from the set of categories based on prevalence of the categories of the set of categories within the events obtained for the entities in the active subgroup. A target category subset (203) is determined based on the model category subset (202) (102). The model category subset (202) in particular comprises the target category subset (203). Preferably, the target category subset is determined from the model category subset based on time spans for initial occurrence of the categories of the model category subset within the events obtained for the entities in the active subgroup. For each entity of the group, for which per category of the target category subset (203) at least one event associated with the category has been obtained, i.e. for which the events obtained for the entity comprise for each category of the target category subset at least one event associated with the category, a sequence of categories of the model category subset (202) is determined based on the events obtained for the entity (103), preferably based on time-ordered occurrence of the categories of the model category subset within the events obtained for the entity. The sequence consists of: a base comprising one or more categories; and a trail category after the base. A base comprising two or more categories is itself a subsequence consisting of: a base comprising one or more categories; and a tail category after the base. For each sequence of the determined sequences and their recursive bases which comprise two or more categories, i.e. for each sequence of the determined sequence and their subsequences, a probability is calculated for the tail category of said sequence to follow the base of said sequence (104). For a target entity of the group of multiple entities, for which for at least one category of the target category subset no events associated with said at least one category have been obtained, i.e. for which the events obtained for the entity comprise for at least one category of the target category subset no events associated with the category, a target sequence of categories of the model category subset is determined based on the events obtained for the target entity (105), preferably based on time-ordered occurrence of the categories of the model category subset within the events obtained for the target entity. A target category of said at least one category is determined based on the target sequence and the calculated probabilities (105). Information based on the target entity and the determined target category is provided (106).

In a preferred embodiment, the CIM comprises the following steps:

obtaining for each entity of a group of multiple entities one or more, preferably multiple, events, each event associated with a time stamp and a category of a set of categories;

calculating for each entity of the group an average event frequency;

determining an active subgroup of entities based on the calculated average event frequencies;

determining a model category subset from the set of categories based on prevalence of the categories of the set of categories within the events obtained for the entities in the active subgroup;

determining a target category subset from the model category subset based on time spans for initial occurrence of the categories of the model category subset within the events obtained for the entities in the active subgroup;

determining for each entity of the group of multiple entities, for which the events obtained for the entity comprise for each category of the target category subset at least one event associated with the category, a sequence of categories of the model category subset based on time-ordered occurrence of the categories of the model category subset within the events obtained for the entity, wherein the sequence consists of:
  a base comprising one or more categories; and
  a tail category after the base,
wherein a base comprising two or more categories is itself a subsequence consisting of:
  a base comprising one or more categories; and
  a tail category after the base, calculating for each sequence of the determined sequences and their subsequences, a probability for the tail category of the sequence to follow the base of the sequence;

determining for a target entity of the group of multiple entities, for which the events obtained for the entity comprise for at least one category of the target category subset no events associated with the category, a target sequence of categories of the model category subset based on time-ordered occurrence of the categories of the model category subset within the events obtained for the target entity and a target category of said at least one category based on the target sequence and the calculated probabilities;

providing information based on the target entity and the determined target category.

Reference is made to the section "Summary of the invention" above for a discussion of several advantages.

In a preferred embodiment, the invention is configured for fault forecasting in an apparatus and information provision. In this embodiment, an entity is an apparatus, whereby the apparatus preferably comprises one or more sensors. An apparatus may be represented by an apparatus id. The one or more events for each apparatus are then preferably obtained based on data from the one or more sensors of the apparatus. In this embodiment, the information is preferably servicing information for fault avoidance. In identical or similar apparatuses, certain symptoms may indicate the arrival of a fault. This may be because the symptoms cause the fault. This may alternatively or additionally be because the symptoms and the fault-to-arrive are caused by a common root cause.

In another embodiment, the invention is configured for forecasting feature usage by a user in a CPP and information provision. In this embodiment, an entity is a user. A user may be represented by a user id. In this embodiment, a category is a feature of the computer program product. In this embodiment, the step of providing information based on the target entity and the target category is preferably the step of providing tutorial information about the target feature via a visualization means to the target user. Upon learning to use a CPP, the amount of new features may be overwhelming to a user. In this embodiment, the present invention provides tutorial information about a target feature to the user, wherein the target feature is specifically selected based on the feature usage history of the user, and may therefore be particularly of interest to the user. This, in turn, may lead to a more time and resource efficient learning process, as the user is not presented with a steep learning curve based on lengthy documentation which is mostly irrelevant, but mostly with relevant tutorials. This may also lead to selective new feature introduction to experienced users upon releasing a new version of a CPP.

In yet another embodiment, the invention is configured for forecasting interaction type by a user with a service and information provision. In this embodiment, an entity is a user, which may by represented by a user id. In this embodiment, a category is an interaction type. In this embodiment, the step of providing information based on the target entity and the target category is the step of providing information on the target interaction type to the user.

In a preferred embodiment, the determination for an entity of a sequence of categories of the model category subset based on the events obtained for the entity is based on the time-ordered occurrence of the categories of the model category subset within the events obtained for the entity. Thereby, a determined sequence for an entity may comprise each category of the model category subset at most once, whereby preferably the determined sequence is based on time-ordered first occurrence of the categories of the model category subset within the events obtained for the entity. Alternatively, a determined sequence for an entity may comprise a category of the model category subset a number of times which is equal to the number of events obtained for said entity which are associated with said category, i.e. the sequence comprises a category of the model category subset as many times as it arises in the associated events obtained for the entity. Recurrence of categories may be important or may be less relevant. For example for CPP feature tutorial presentation, repetitive usage of a feature or feature sequence may be indicative that a user would benefit from a particular other feature, while single usage may be indicative of a try-out or error. For example for fault forecasting for an apparatus, a positive correlation may exist between a category and a fault, whereby the fault likelihood is further independent of the number of occurrences of the particular category.

The step of determining a target category subset and a model category subset of the set of categories may comprise one or more of the following steps. Preferably, for each entity of the group an average frequency is calculated. Preferably, an active subgroup of entities is determined based on the calculated average event frequencies. The active subgroup of entities preferably comprises the entities for which the calculated average event frequency is larger than or not smaller than a predefined frequency cut-off value. Preferably, the model category subset of the set of categories is determined based on category occurrence, preferably within the events obtained for the entities in the active subgroup. Preferably, the model category subset is determined from the set of categories based on prevalence of the categories of the set of categories within the events obtained for the entities in the active subgroup. Preferably, for each category of the set of categories an average category frequency is calculated, preferably based on the events obtained for the entities in the active subgroup. Preferably, the model category subset is determined based on a predefined number or predefined percentage of categories of the set of categories with the largest calculated average category frequencies, preferably over the events obtained for the entities in the active subgroup. The target category subset is then determined from the model category subset, whereby the model category subset comprises the target category subset.

The step of determining a target category subset and a model category subset of the set of categories may comprise one or more of the following steps. Preferably, for each entity of the group an average frequency is calculated. Preferably, an active subgroup of entities is determined based on the calculated average event frequencies. The active subgroup of entities preferably comprises the entities for which the calculated average event frequency is larger than or not smaller than a predefined frequency cut-off value. A model category subset of the set of categories is determined, preferably as described above. Preferably, for each category of the model category subset, an average time span for initial occurrence of an event associated with the category, preferably over the active subgroup of entities, is calculated. Preferably, the target category subset is determined from the model category subset based on the determined average time spans for the categories of the model category subset. Preferably, the target category subset is determined from the model category subset based on time spans for initial occurrence of the categories of the model category subset within the events obtained for the entities in the active subgroup. Preferably, the target category subset is determined based on a predefined number or predefined percentage of categories of the model category subset with the smallest determined average time spans.

The step of calculating for each sequence of the determined sequences and their recursive bases which comprise two or more categories, i.e. for each sequence of the determined sequences and their subsequences, a probability for the tail category of said sequence to follow the base of said sequence may comprise one or more of the following steps. Preferably, an input list of input sequences is obtained. Preferably, the input list comprises the determined sequences. Preferably, the input list furthermore comprises per determined sequence all corresponding recursive bases which comprise two or more categories once, i.e. the input list furthermore comprises per determined sequence all corresponding subsequences once. Preferably, an output list is obtained. Preferably, the output list comprises all unique bases of the input sequences of the input list. The output list preferably comprises all unique bases of the input sequences of the input list once. Preferably, for each base of the output list, a predecessor number is determined. Preferably, the predecessor number of a base is the number of input sequences in the input list of which it is the base. Preferably, for an input sequence of the input list, more preferably for each input sequence of the input list, a probability for the tail category of said input sequence to follow the base of said input sequence is calculated, preferably based on the number of occurrences of said input sequence in the input list and the corresponding predecessor number of its base in the output list. Preferably, the probability for the tail category of an input sequence to follow the base of the input sequence is calculated by dividing the number of occurrences of said input sequence in the input list by the corresponding predecessor number for its base in the output list.

In a preferred embodiment, an event comprises a communication channel of a collection of communication channels. A target communication channel of the collection is determined for the target entity. The information based on the target entity and the determined target category is preferably provided via the target communication channel. In a first further embodiment, a category may comprise a communication channel, and the target communication channel may be determined via determination of the target category. In a second alternative further embodiment, a sequence of communication channels or a sequence of pairs of a category and a communication channel may be used for determining a target communication channel.

The invention is further described by the following non-limiting examples which further illustrate the invention, and are not intended to, nor should they be interpreted to, limit the scope of the invention.

EXAMPLES

Example 1: Embodiment According to the Present Invention

For each entity of a group of multiple entities, one or more events are obtained. Each event is associated with a time stamp and a category of a set of categories. A category has "occurred" for an entity, when an event associated with the category has been obtained for the entity. A category has "not yet occurred" for an entity, when no events associated with the category have been obtained for the entity.

Model and Target Category Subset

For each entity of the group, an average event frequency is calculated. The average event frequency for an entity may for example be the average number of events per month for said entity in the last year, or in case the entity is not yet active during a full year, it may be the average number of events per month for said entity during its active time span. An active subgroup of active entities is determined. "Active entities" are entities for which the calculated average event frequency is larger than or not smaller than a predefined frequency cut-off value. Other entities are called "inactive entities".

The events obtained for the active entities (of the active subgroup) are filtered out. For each category of the set of categories, an average active category frequency is calculated based on the filtered events, i.e. the events of the active entities in the active subgroup. An average active category frequency may for example be the average number of occurrences of the category per active entity per month. The model category subset is determined from the set of categories based on a predefined number or predefined percentage of categories of the set of categories with the largest calculated average active category frequencies. The categories of the set of categories may for example be ordered in a first selection list according to calculated average active category frequency, and depending on whether increasing or decreasing ordering is utilized, the bottom or top part of categories of the first selection list, based on a predefined number of predefined frequency, are retained as the model category subset of the set of categories. Categories of the model category subset are further also referred to as model categories.

For each model category, an average time span for initial occurrence (of an event associated with the model category) is determined over the active subgroup of active entities. Preferably, for active entities for which a model category has not yet occurred, either a predefined default time span value is utilized for determining the average time span for initial occurrence, or these active entities are not taken into account for determining the average time span for initial occurrence, most preferably the latter. The target category subset is determined from the model category subset based on the determined average time spans for initial occurrence for the model categories of the model category subset. Preferably, the target category subset is based on a predefined number or predefined percentage of model categories of the model category subset with the smallest determined average time spans for initial occurrence. The model categories of the model category subset may for example be ordered in a second selection list according to determined average time span for initial occurrence, and depending on whether increasing or decreasing ordering is utilized, the top or bottom part of model categories of the second selection list, based on a predefined number of predefined frequency, are retained as the target category subset of the model category subset. Categories of the target category subset are further also referred to as target categories.

Forecasting Model Building

A full-track subgroup of full-track entities is determined. An entity is a full-track entity when for each target category of the target category subset at least one event associated with the target category has been obtained, i.e. when each target category has occurred for the entity. An entity for which for at least one target category of the target category subset no events associated with said at least one category have been obtained, i.e. an entity for which at least one target category has not yet occurred, is called a partial-track entity. One of ordinary skill will appreciate that each of the following four cases may arise: an active full-track entity, an inactive full-track entity, an active partial-track entity, and an inactive partial-track entity.

For each full-track entity of the group, a sequence of model categories of the model category subset is determined based on the events obtained for the full-track entity. The sequence is thereby determined based on time-ordered occurrence of the model categories within the events obtained for the full-track entity. A determined sequence may thereby comprise each model category at most once, whereby the model categories of the determined sequence are ordered according to time-ordered first occurrence of the model categories of the model category subset within the events obtained for the full-track entity, in particular according to the time stamps of the events, i.e. only first occurrence of a model category is represented in the determined sequence. A determined sequence may thereby alternatively comprise a model category a number of times which is equal to the number of events obtained for the full-track entity which are associated with the model category, i.e. each occurrence of a model category for the full-track entity is represented in its determined sequence.

For each sequence of the determined sequences and their recursive bases which comprise two or more categories (and which bases are therefore also sequences), a probability for the tail category of said sequence to follow the base of said sequence is calculated. The following steps are thereby most preferably utilized for said calculation of said probabilities. An input list of input sequences is obtained. The input list comprises the determined sequences. The input list furthermore comprises per determined sequence all corresponding recursive bases which comprise two or more categories once. An output list is obtained. The output list comprises all unique bases of the input sequences of the input list once. For each base of the output list, the predecessor number of input sequences in the input list of which it is the base is determined. For each input sequence of the input list, a probability for the tail category of said input sequence to follow the base of said input sequence is calculated by dividing the number of occurrences of said input sequence in the input list by the corresponding predecessor number for its base in the output list.

Forecasting for a Partial-Track Entity

For a target partial-track entity, a target sequence of model categories of the model category subset is determined based on the events obtained for the target entity. The sequence is thereby determined based on time-ordered occurrence of the model categories within the events obtained for the target partial-track entity. A determined sequence may thereby comprise each model category at most once, whereby the model categories of the determined sequence are ordered according to time-ordered first occurrence of the model categories of the model category subset within the events obtained for the target partial-track entity, in particular according to the time stamps of the events, i.e. only first occurrence of a model category is represented in the determined sequence. A determined sequence may thereby alternatively comprise a model category a number of times which is equal to the number of events obtained for the target partial-track entity which are associated with the model category, i.e. each occurrence of a model category is represented in the determined sequence.

For the target partial-track entity, a target category is determined based on the target sequence and the calculated probabilities. The determined target category is in particular a category of the target category subset for which no events associated with the target category have been obtained for the target partial-track entity. Occurrence of the determined target category for the target partial-track entity would therefore bring the target partial-track entity 'closer' to becoming a full-track entity. Preferably, the determined target category comprises the largest probability according to the calculated probabilities to follow the target sequence.

Information Provision

Information based on the target partial-track entity and the determined target category are provided.

Example 2: User Engagement

The present example builds further on example 1, and relates to user interaction with an organization. An entity is a user. A category is also referred to as an event type. A model category is also referred to as a waypoint. A target category is also referred to as a milestone. A sequence (of model categories) is also referred to as a journey (of waypoints). A base is also referred to as a sub-journey. A full-track entity is also referred to as an onboarded user. A partial-track entity is also referred to as a pre-onboarded user.

Figure 3:
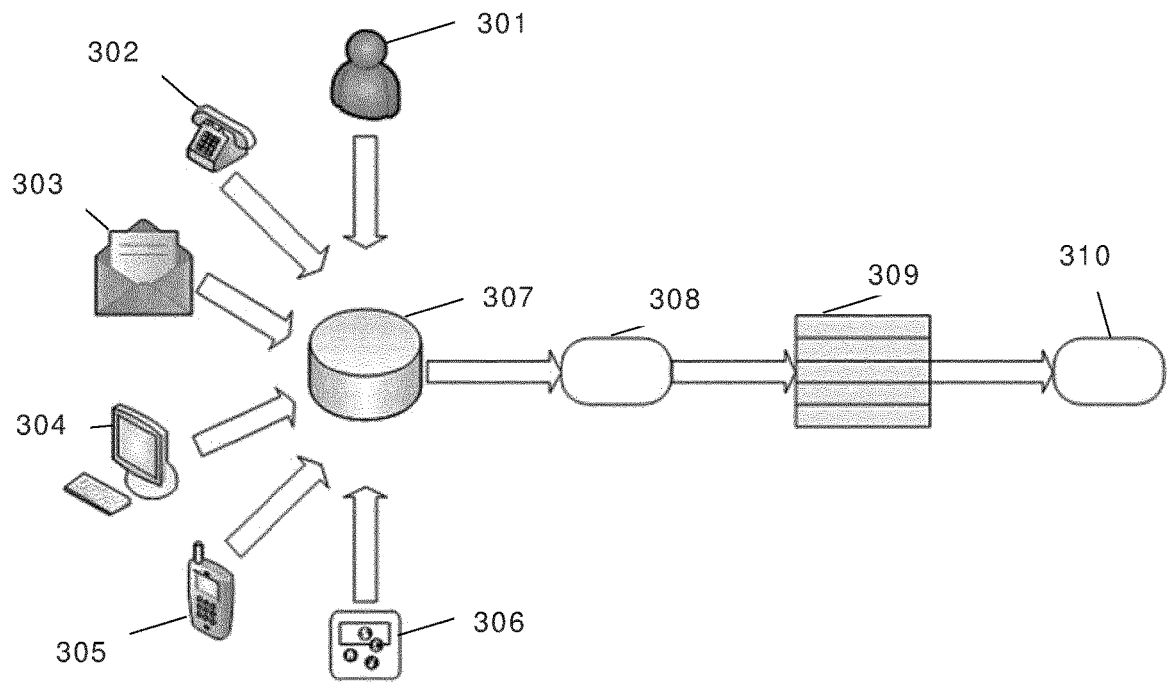
FIG. 3 shows a schematic overview of communication channels and data processing, according to an embodiment of the present invention.

FIG. 3 shows a schematic overview of communication channels and data processing, according to an embodiment of the present example. Users may interact with the organization through six communication channels: face-to-face interaction (301), telephone (302), mail (303), online via the organization's web platform and/or e-mail (304), mobile via the organization's mobile or web platform (305), and debit and credit card transactions (306). Each interaction of a user may be recorded within one of several systems, based on a unique user id associated with the user. Periodically, preferably at the beginning of each day, the recorded data from the previous period, preferably previous day, may be extracted from storage, transformed into the correct format, and loaded into a relational database (307).

New data in the relational database (307) may be transformed (308), preferably daily, into events, which are added to an event log (309). An event comprises a user id, an event type (category) of a set of event types, and a date (time stamp). The event log (309) can be queried for events for usage in an algorithm (310) according to the present invention.

For each user id, the average number of events per month (average event frequency) is determined. User ids associated with an average number of events on or above a predefined threshold (predefined frequency cut-off value) are flagged as active. All other user ids are flagged as inactive. The predefined threshold may be adjusted via a user input device.

In order to obtain a workable predictive algorithm, in particular on a computing system comprising a finite or limited amount of resources, the number of variables or degrees of freedom is reduced. A model category subset of waypoints (model categories) is selected. The waypoints are selected by calculating the average number of times each event type occurs per active user id, and flagging the most frequent ones as waypoints. The motivation for this selection is that the more frequently an event type occurs within a group of users, the more important that event type is to that group of users. The events of the active user ids are filtered out, the average monthly frequency of each event type within the active subgroup of active users is calculated, and a model category subset comprising a predefined number of waypoints is outputted. The waypoints are the event types with largest average monthly frequency. The predefined number of waypoints may be adjusted via a user input device.

Figure 4:
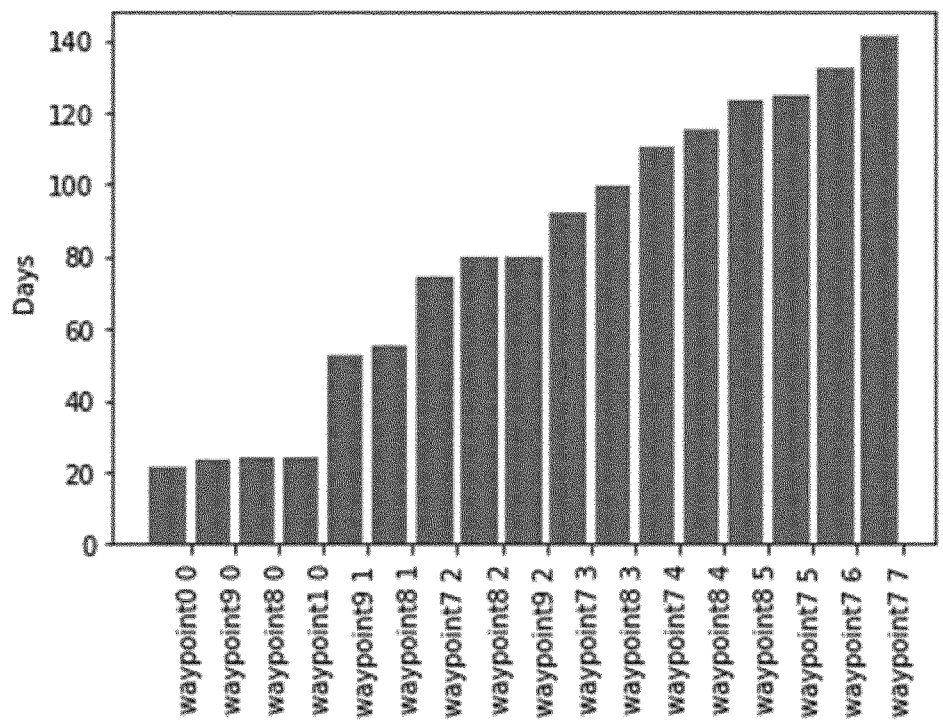
FIG. 4 shows a chart showing average time span for initial occurrence for categories of the model category subset, according to an embodiment of the present invention.

A target category subset of milestones is selected from the model category subset of waypoints. The average amount of time between the date a user joins the organization and the occurrence of a waypoint (average time span for initial occurrence) for the user is determined. FIG. 4 shows an exemplary chart showing average time span for initial occurrence of waypoints, in increasing order of average time span. Waypoint00 may be selected as a milestone, since it takes the smallest number of days (on average) for occurrence for a user. The selection criterion of smallest determined average time spans for initial occurrence reflects the timeliness for intervention via information provision. For other purposes, other criteria may be utilized.

An onboarded user id is associated with a user who has 'achieved' all milestones, i.e. for which the event log comprises for each milestone at least one event comprising the user id and the milestone. A pre-onboarded user id is associated with a user who has 'not achieved' all milestones, i.e. for which the event log lacks for at least one milestone an event comprising the user id and the milestone. The following procedure is preferably utilized for determining which user ids are onboarded and which user ids are pre-onboarded. A data table is created, comprising a column with user ids, as well as a column per waypoint. An entry of the data table corresponding with a column and a user id comprises the date of the event on which the corresponding user has first achieved the waypoint. In case a waypoint is not yet achieved by a user, the corresponding entry of the data table comprises a null entry. Per row, the columns associated with milestones are looped, and in case a null is detected, the user id is flagged as pre-onboarded. Otherwise the user id is flagged as onboarded. An additional column of the data table is filled with the flags. The data table is then split into two data tables: an onboarded data table comprising the entries of the onboarded user ids, and a pre-onboarded data table comprising the entries of the pre-onboarded user ids.

Figure 7:
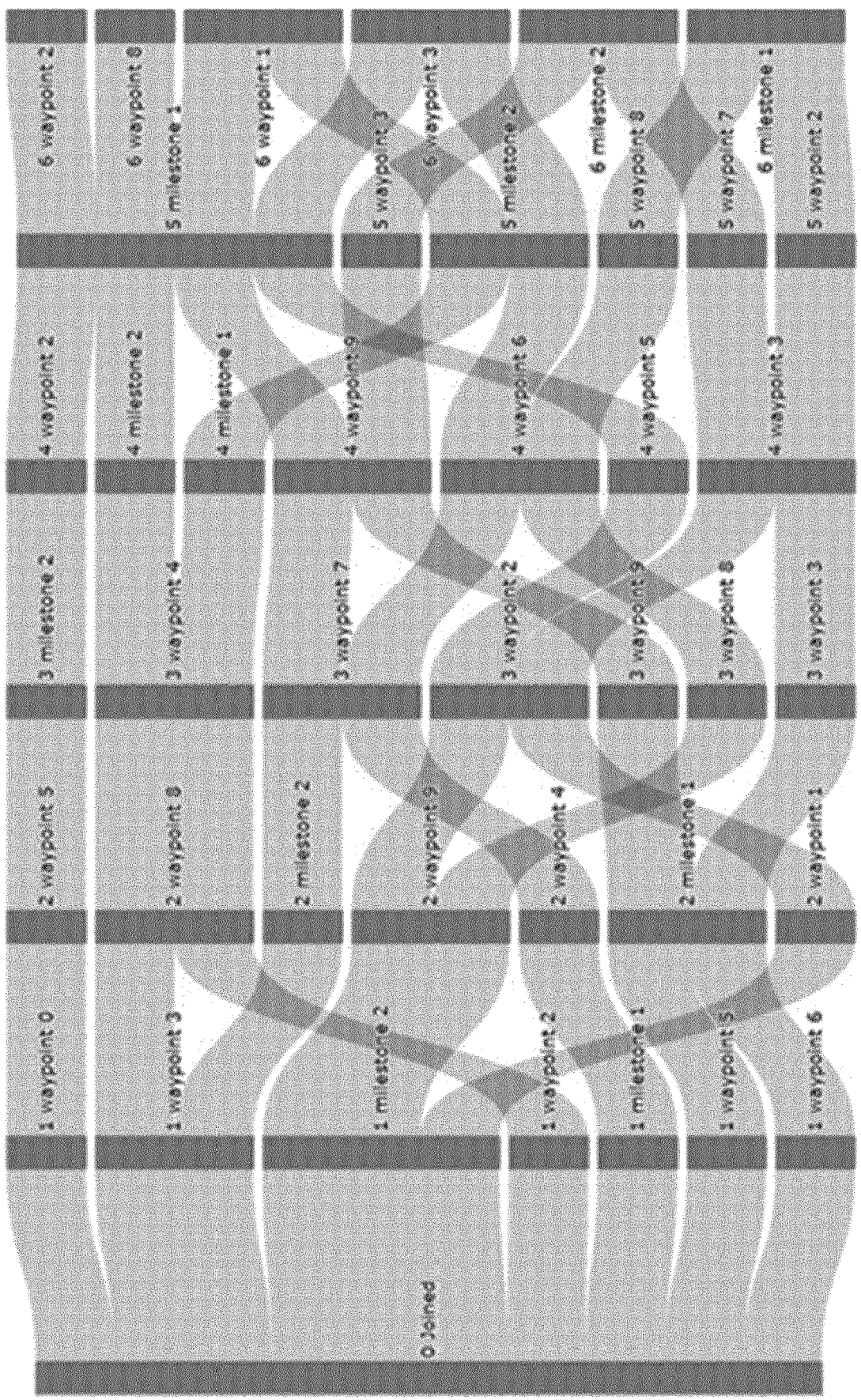
FIG. 7 shows a schematic overview of sequences, according to an embodiment of the present invention.

The onboarded data table is then utilized to build a predictive model for the pre-onboarded user ids. For each user id, the first occurrences of waypoints are mapped in chronological order. For onboarded user ids, in addition to the journeys, also all sub-journeys comprising two or more waypoints are determined. This may be achieved by separating the waypoints of the journey and incrementally adding one at a time, in order, until the journey is obtained again. An input list comprising all journeys and sub-journeys of length at least two is obtained. An output list comprising all unique bases of the sequences in the input list is determined. The (predecessor) number of sequences (journeys and sub-journeys of length at least two) in the input list corresponding to each unique base is determined and added to a separate list. Next, the number of occurrences of each unique sequence of the input list is determined, and divided by the predecessor number of the corresponding base. This results in the counting probability of each unique sequence of the input list over the onboarded group of onboarded users. A probability list may be obtained comprising per unique journey and sub-journey of the onboarded user ids the calculated probability. The probability list may be visually represented in a Sankey plot, an example of which is shown in FIG. 7.

Figure 6:
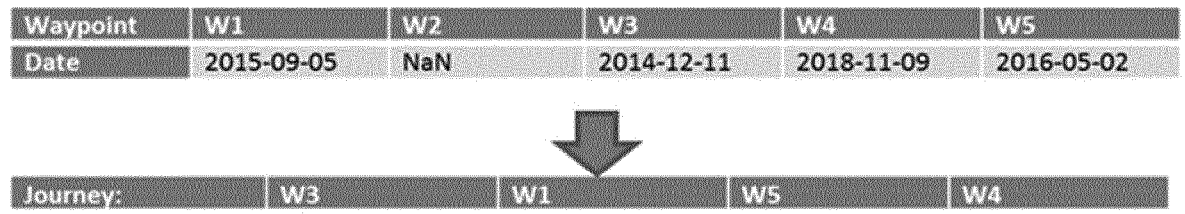
FIG. 6 shows a schematic overview of a sequence of categories of the model category subset based on events of an entity, according to an embodiment of the present invention.

Reference is made to FIG. 6. Suppose for user id x, the entry of the data table for waypoint W1 comprises the date 2015-09-05, the entry of the data table for waypoint W2 comprises a null entry, the entry of the data table for waypoint W3 comprises the date 2014-12-11, the entry of the data table for waypoint W4 comprises the date 2018-11-09, and the entry of the data table for waypoint W5 comprises the date 2016-05-02, then the journey for user id x may be determined as W3→W1→W5→W4. In case user id x is an onboarded user id, the sub-journeys W3→W1→W5 and W3→W1 are also determined. Suppose for user id y, the journey W3→W1→W4→W5 is determined, as well as the sub-journeys W3→W1→W4 and W3→W1. The input list may then be [W3→W1; W3→W1→W5; W3→W1→W5→W4; W3→W1; W3→W1→W4; W3→W1→W4→W5]. The output list may then be [W3; W3→W1; W3→W1→W5; W3→W1→W4] with corresponding predecessor number list [2; 2; 1; 1]. The probability of the sequence W3→W1→W4 is then ½=0.5.

Figure 5:
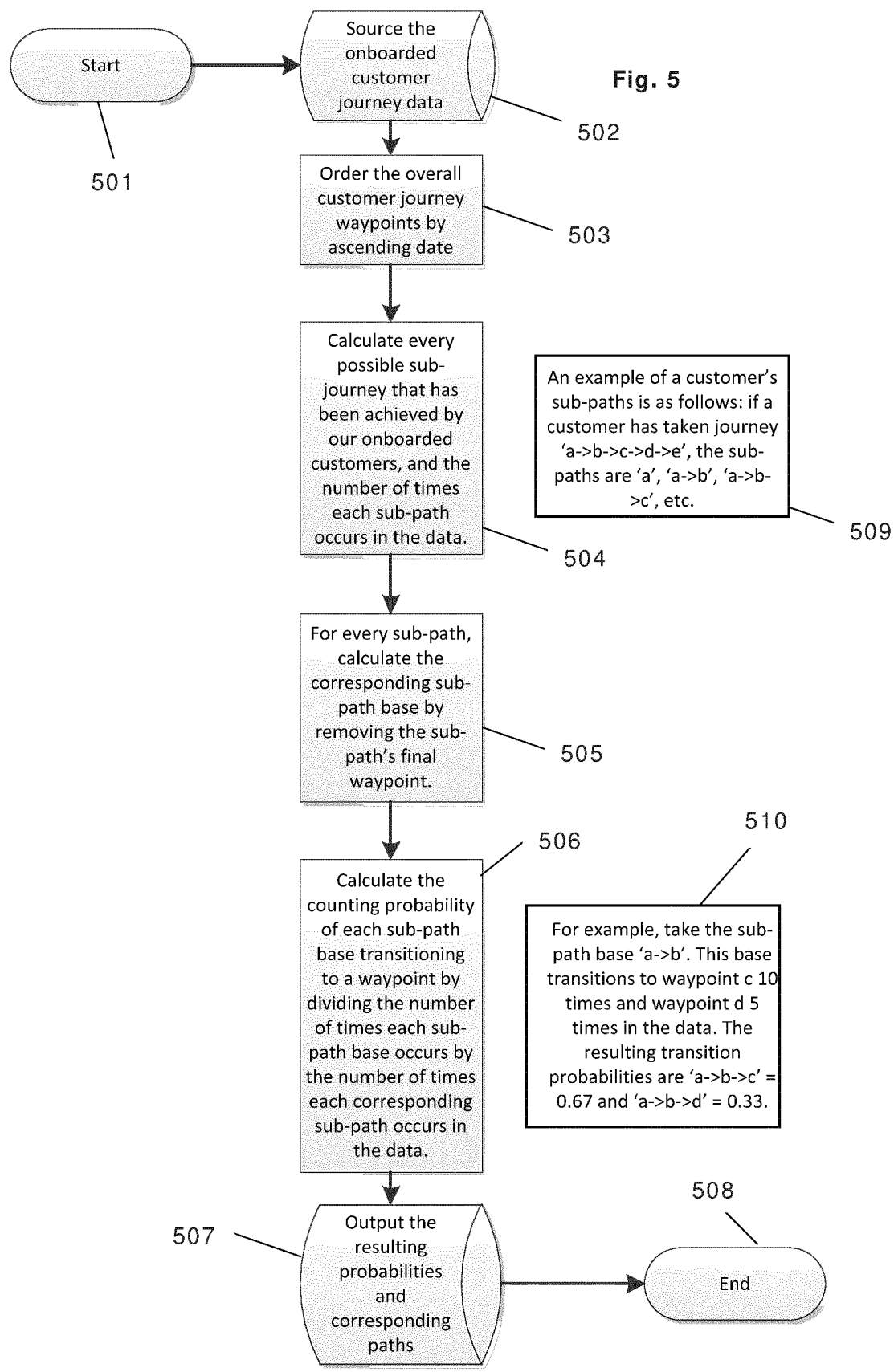

FIG. 5 shows a schematic overview of an embodiment of an algorithm to calculate the probability for a sequence, which may be performed from start (501) to end (508). The onboarded user journey data may be sourced (502). The onboarded user journey waypoints may be ordered by ascending dates (503). Every possible sub-journey that has been achieved by onboarded users may be calculated, and the number of times each sequence occurs in the data (504). If for a user id the journey a→b→c→d→e has been obtained, the sub-journeys are a, a→b, a→b→c, and a→b→c→d (509). The sub-journeys of length at least two are a→b, a→b→c, and a→b→c→d. For each sequence (journey or sub-journey of length at least two), the base is determined by removing the sequence's final waypoint (505). The counting probability of each base transitioning to a waypoint is calculated by dividing the number of times each sequence occurs by the predecessor number of its corresponding base (506). If, for example, the base a→b transitions to waypoint c 10 times and to waypoint d 5 times, the resulting transition probabilities are 0.6666 . . . for a→b→c and 0.3333 . . . for a→b→d. The corresponding sequences and probabilities are outputted (507) in a probability list.

For a pre-onboarded user id, a target sequence may be determined based on the pre-onboarded data table. The transition probability to each milestone which the corresponding user has not yet achieved, is determined based on the calculated probabilities, i.e. it is read from the probability list if present and set to zero otherwise. The milestone corresponding with a largest probability is selected.

Example 3: Information Provision

The present example builds further on examples 1 and 2.

Once milestones have been predicted for a pre-onboarded group of pre-onboarded users, the users are contacted. The pre-onboarded group may comprise pre-onboarded users for which a particular milestone has been predicted. The pre-onboarded group may comprise all pre-onboarded users. The pre-onboarded group may comprise pre-onboarded users which have not been contacted recently, i.e. within a predefined contact time span. Contact data of a user may comprise first and second name, home address, e-mail address, telephone number, and/or mobile telephone number. Via an SQL query based on the user id, a predicted milestone may be linked with corresponding contact data. The query can in particular be filtered for one or more particular pieces of contact information. The contact information may be associated with a particular event type. For example, in case the milestone is usage of a mobile platform, the relevant contact information may a telephone number for sending an SMS. In this case, the first name, second name, and telephone number are obtained.

Figure 8:
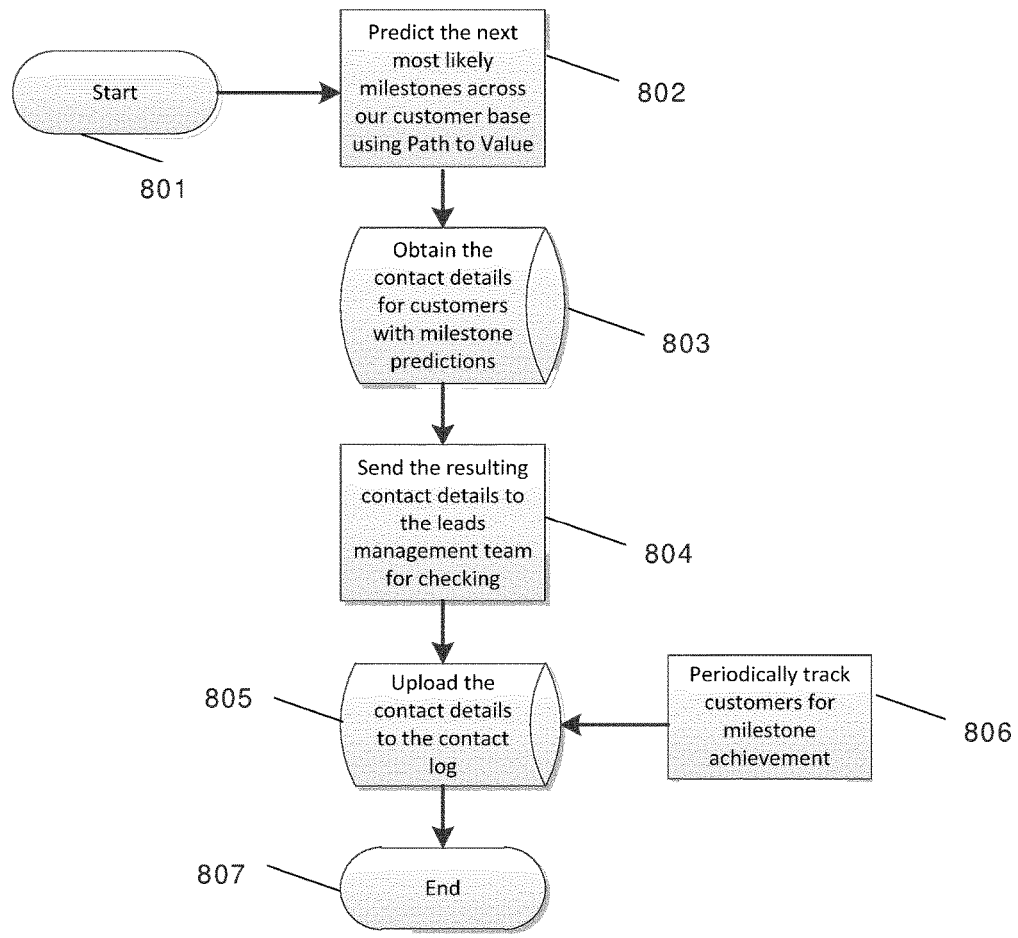

FIG. 8 shows an outline of an algorithm for user contacting, which may be performed from start (801) to end (807). For each pre-onboarded user id, the next most likely milestone is predicted as described in example 2 above (802). The contact details for user ids with milestone predictions are obtained (803). The resulting contact details are sent to a verification team (804). Upon verification, the contact details are uploaded to a contact log (805). Based on the contact log, users are contacted. Contacted users are periodically tracked, in particular with regard to achievement of predicted and/or other milestones (806).

Contact information may be tested via one or more test functions. In case not all test functions pass, manual intervention may be requested. In case all test functions pass, contact information may be exported as an excel file for sending to a contact centre.

Figure 9:
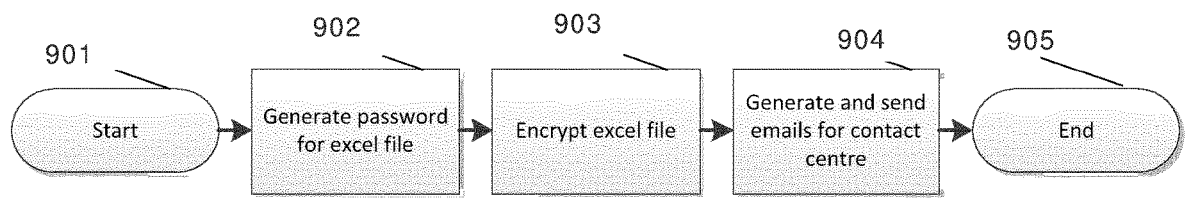

FIG. 9 shows an algorithm comprising steps, which may be involved in creating and e-mailing user contact details to the contact centre, and which may be performed from start (901) to end (905). A 6-character password may be randomly generated (902). The excel file may by encrypted based on the password (903). An e-mail comprising the encrypted excel file may be sent to the contact centre (904).

The password may be provided to the contact centre via another communication channel of via another e-mail (904).

An event comprising a user id and an event type, whereby the event type is associated with contacting, may be added to the event log.

Example 4: Assessment of Performance of an Algorithm

The present example builds further on examples 1, 2 and 3.

A control group of users has been obtained, which is non-overlapping with the (prediction) group of users. For the users of the control group, a not yet achieved milestone is randomly assigned. The users of the control group are also contacted in relation to the randomly selected milestone. By comparing results for the group of users with results for the control group of users, performance of the present invention has been assessed.

Performance may be assessed based on the achievement of the predicted or randomly selected milestone by a user, either within a predefined time window or as next waypoint. Preferably, and in the present example, performance has been assessed based on the achievement of the predicted or randomly selected milestone within a predefined time window from contacting, especially within the context of the present example a predefined time window of three months from contacting.

Figure 10:
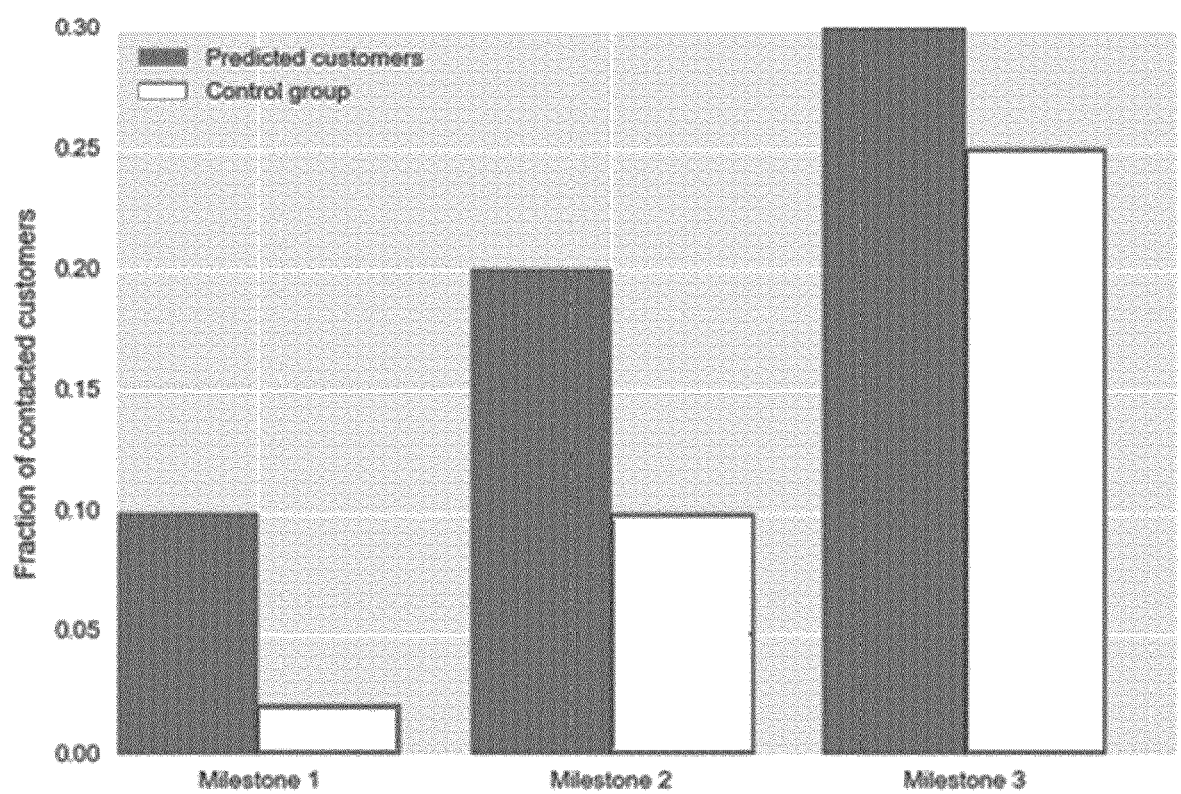
FIG. 10 shows a chart showing success rate of a stimulated group of entities versus a control group of entities, according to an embodiment of the present invention.

FIG. 10 shows a chart showing fraction of contacted users meeting the achievement of the predicted (dark bars) or randomly selected (white bars) milestone, per milestone, and for the control group (white bars) and prediction group (dark bars) separately. It may be observed that users are significantly more likely to achieve a predicted milestone than a randomly selected milestone.

The invention claimed is:

1. Computer-implemented method for event forecasting and information provision, comprising the steps of:
obtaining for each entity of a group of multiple entities one or more, preferably multiple, events, each event associated with a time stamp and a category of a set of categories;
calculating for each entity of the group an average event frequency;
determining an active subgroup of entities based on the calculated average event frequencies;
determining a model category subset from the set of categories based on prevalence of the categories of the set of categories within the events obtained for the entities in the active subgroup;
determining a target category subset from the model category subset based on time spans for initial occurrence of the categories of the model category subset within the events obtained for the entities in the active subgroup;
determining for each entity of the group of multiple entities, for which the events obtained for the entity comprise for each category of the target category subset at least one event associated with the category, a sequence of categories of the model category subset based on time-ordered occurrence of the categories of the model category subset within the events obtained for the entity, wherein the sequence consists of: a base comprising one or more categories; and a tail category after the base, wherein a base comprising two or more categories is itself a subsequence consisting of: a base comprising one or more categories; and a tail category after the base;
calculating for each sequence of the determined sequences and their subsequences, a probability for the tail category of the sequence to follow the base of the sequence;

determining for a target entity of the group of multiple entities, for which the events obtained for the entity comprise for at least one category of the target category subset no events associated with the category, a target sequence of categories of the model category subset based on time-ordered occurrence of the categories of the model category subset within the events obtained for the target entity and a target category of said at least one category based on the target sequence and the calculated probabilities;

providing information based on the target entity and the determined target category.

2. Computer-implemented method according to preceding claim 1, wherein a determined sequence for an entity comprises each category of the model category subset at most once, preferably wherein the determined sequence is based on time-ordered first occurrence of the categories of the model category subset within the events obtained for the entity.

3. Computer-implemented method according to preceding claim 1, wherein a determined sequence for an entity comprises a category of the model category subset a number of times which is equal to the number of events obtained for said entity which are associated with said category.

4. Computer-implemented method according to claim 1, wherein the step of determining the model subset from the set of categories based on prevalence of the categories of the set of categories within the events obtained for the entities in the active subgroup comprises the steps of:
    calculating for each category of the set of categories an average category frequency based on the events obtained for the entities in the active subgroup;
    determining the model category subset based on a predefined number or predefined percentage of categories of the set of categories with the largest calculated average category frequencies.

5. Computer-implemented method according to claim 1, wherein the step of determining a target category subset from the model category subset based on time spans for initial occurrence of the categories of the model category subset within the events obtained for the entities in the active subgroup comprises the steps of:
    calculating for each category of the model category subset an average time span for initial occurrence of an event associated with the category over the active subgroup of entities;
    determining the target category subset based on a predefined number or predefined percentage of categories of the model category subset with the smallest determined average time spans.

6. Computer-implemented method according to claim 1, wherein the active subgroup of entities comprises the entities for which the calculated average event frequency is larger than or not smaller than a predefined frequency cut-off value.

7. Computer-implemented method according to claim 1, wherein the step of calculating for each sequence of the determined sequences and their subsequences, a probability for the tail category of the sequence to follow the base of the sequence, comprises the steps of:
    obtaining an input list of input sequences comprising the determined sequences and per determined sequence all corresponding subsequences once;
    obtaining an output list comprising all unique bases of the input sequences of the input list;
    determining for each base of the output list the predecessor number of input sequences in the input list of which it is the base;
    calculating for each input sequence of the input list a probability for the tail category of said input sequence to follow the base of said input sequence by dividing the number of occurrences of said input sequence in the input list by the corresponding predecessor number for its base in the output list.

8. Computer-implemented method according to claim 1, wherein an event comprises a communication channel of a collection of communication channels, wherein the method comprises the step of determining for the target entity a target communication channel of the collection, wherein the information based on the target entity and the determined target category is provided via the target communication channel.

9. Computer-implemented method for fault forecasting in an apparatus and information provision, according to claim 1, wherein an entity is an apparatus comprising one or more sensors, wherein the one or more events for each apparatus are obtained based on data from the one or more sensors of the apparatus, and wherein the information is servicing information for fault avoidance.

10. Computer-implemented method for forecasting feature usage by a user in a computer program product and information provision, according to claim 1, wherein an entity is a user, wherein a category is a feature of the computer program product, and wherein the step of providing information based on the target entity and the target category is the step of providing tutorial information about the target feature via a visualization means to the target user.

11. Computer-implemented method for forecasting interaction type by a user with a service and information provision, according to claim 1, wherein an entity is a user, wherein a category is an interaction type, and wherein the step of providing information based on the target entity and the target category is the step of providing information on the target interaction type to the user.

12. Computer system for event forecasting and information provision, wherein the computer system is configured for carrying out the computer-implemented method according to claim 1.

13. A non-transitory computer readable medium comprising program instructions for causing an apparatus to perform at least the following: the computer-implemented method according to claim 1.

* * * * *